(12) United States Patent
Radojicic

(10) Patent No.: US 10,478,555 B2
(45) Date of Patent: Nov. 19, 2019

(54) SYSTEMS AND METHODS FOR LUMBAR CEREBROSPINAL FLUID ACCESS AND TREATMENT

(76) Inventor: Milan Radojicic, Los Gatos, CA (US)

( * ) Notice: Subject to any disclaimer, the term of this patent is extended or adjusted under 35 U.S.C. 154(b) by 826 days.

(21) Appl. No.: 12/857,555

(22) Filed: Aug. 16, 2010

(65) Prior Publication Data

US 2010/0312084 A1    Dec. 9, 2010

Related U.S. Application Data

(63) Continuation-in-part of application No. 12/228,697, filed on Aug. 16, 2008, now Pat. No. 9,770,180.
(Continued)

(51) Int. Cl.
*A61M 5/172* (2006.01)
*A61M 25/00* (2006.01)
(Continued)

(52) U.S. Cl.
CPC .......... *A61M 5/1723* (2013.01); *A61M 25/00* (2013.01); *A61M 27/006* (2013.01);
(Continued)

(58) Field of Classification Search
CPC .. A61M 5/1723; A61M 25/00; A61M 27/006; A61M 2025/0002;
(Continued)

(56) References Cited

U.S. PATENT DOCUMENTS

| 4,583,968 A | 4/1986 | Mahurkar |
| 4,904,237 A | 2/1990 | Janese |

(Continued)

OTHER PUBLICATIONS

Aygok, Gunes A., et al., "Cerebrospinal Fluid Infusion Studies: Current View and Concepts in Assessment of Post-Traumatic Hydrocephalus", International Brain Injury Association, Issue Apr. 2010, 3 pages.
(Continued)

*Primary Examiner* — Brandy S Lee

(57) ABSTRACT

A system and method for accessing and treating the cerebrospinal fluid with a multilumen catheter configured for placement along a cerebrospinal fluid pathway and a subcutaneous, dual reservoir/pump. The subcutaneous dual reservoir/pump allows simultaneous, bidirectional cerebrospinal fluid access and cerebrospinal fluid exchange. The two chambers prevent mixing of newly treated and discardable cerebrospinal fluid. The subcutaneous dual reservoir/pump can be used inline with other cerebrospinal fluid devices. The catheter may be coupled with a medical probe that sends a wire to a computational device, which can then send wireless data and receive wireless instructions. A method of assessing cerebrospinal fluid infections is provided, whereby monitoring of the cerebrospinal glucose concentrations with a cerebrospinal glucose sensor and analysis of the data by a computational device can notify a patient or medical provider of an impending infection. This assembly can help better diagnose and treat injury and disease.

15 Claims, 11 Drawing Sheets

Related U.S. Application Data which is a continuation-in-part of application No. 11/840,213, filed on Aug. 16, 2007, now abandoned.

(60) Provisional application No. 60/822,640, filed on Aug. 17, 2006, provisional application No. 61/234,144, filed on Aug. 14, 2009.

(51) Int. Cl.
*A61M 27/00* (2006.01)
*A61B 5/03* (2006.01)
*A61B 5/145* (2006.01)
*A61B 5/00* (2006.01)
*A61M 5/142* (2006.01)
*A61M 39/02* (2006.01)

(52) U.S. Cl.
CPC ........... *A61B 5/032* (2013.01); *A61B 5/14532* (2013.01); *A61B 5/7214* (2013.01); *A61M 5/1428* (2013.01); *A61M 39/0208* (2013.01); *A61M 2005/1726* (2013.01); *A61M 2025/0002* (2013.01); *A61M 2025/0057* (2013.01); *A61M 2210/1003* (2013.01); *A61M 2230/201* (2013.01)

(58) Field of Classification Search
CPC .. A61M 2025/0007; A61M 2025/0034; A61M 2025/0037; A61M 2025/0039; A61M 2025/0166; A61M 2025/024; A61M 2210/069; A61M 2210/1003; A61M 25/0021; A61M 25/003; A61M 25/0041; A61M 25/02; A61M 25/0662; A61M 25/10; A61M 25/1011; A61M 2005/1726; A61M 2025/0057; A61M 2230/201; A61M 39/0208; A61M 5/1428; A61M 25/0194; A61M 2202/0464; A61B 5/032; A61B 5/14532; A61B 5/7214
USPC .......................... 604/151, 154, 432
See application file for complete search history.

(56) References Cited

U.S. PATENT DOCUMENTS

| | | | |
|---|---|---|---|
| 5,154,693 A * | 10/1992 | East | A61M 27/002 137/512 |
| 5,221,256 A | 6/1993 | Mahurkar | |
| 5,325,865 A | 7/1994 | Beckman et al. | |
| 5,378,230 A | 1/1995 | Mahurkar | |
| 5,599,301 A | 2/1997 | Jacobs et al. | |
| 5,686,289 A | 11/1997 | Humes et al. | |
| 5,827,237 A | 10/1998 | Macoviak et al. | |
| 6,626,902 B1 * | 9/2003 | Kucharczyk et al. | 606/41 |
| 7,150,737 B2 | 12/2006 | Purdy et al. | |
| 2002/0082556 A1 | 6/2002 | Cioanta et al. | |
| 2003/0097082 A1 * | 5/2003 | Purdy | A61B 17/12136 600/594 |
| 2004/0087863 A1 | 5/2004 | Eide | |
| 2004/0193045 A1 * | 9/2004 | Scarborough et al. | 600/432 |
| 2005/0020962 A1 | 1/2005 | Reich et al. | |
| 2005/0137579 A1 * | 6/2005 | Heruth | A61M 5/14276 604/536 |
| 2005/0171452 A1 | 8/2005 | Neff | |
| 2006/0047201 A1 | 3/2006 | Eide | |
| 2007/0179427 A1 | 8/2007 | Radojicic | |
| 2007/0270782 A1 | 11/2007 | Miesel et al. | |
| 2008/0243074 A1 | 10/2008 | Miesel et al. | |
| 2009/0227025 A1 | 9/2009 | Nichols et al. | |
| 2010/0274221 A1 | 10/2010 | Sigg et al. | |
| 2011/0004304 A1 | 1/2011 | Tao et al. | |
| 2011/0060265 A1 | 3/2011 | Dragoon et al. | |

OTHER PUBLICATIONS

Bateman, Grant A., "The Role of Altered Impedance in the Pathophysiology of Normal Pressure Hydrocephalus, Alzheimer's Disease and Syringomyelia", Medical Hypothesis 63, Apr. 2004, pp. 980-985.

Bazzett et al., "A Novel Device for Chronic Intracranial Drug Delivery via Microdialysis", Journal of Neuroscience Methods, vol. 40, Mar. 1991, pp. 1-8.

Bell, Rodney D., et al., "Ventriculo-Lumbar Perfusion in Acute Ischemic Stroke" Neurocritical Care, 2006; vol. 5, pp. 21-29.

Czosnyka et al., "Cerebrospinal fluid dynamics." Physiological measurement, vol. 25, Oct. 2004, R51-76.

El Sankari et al., "Cerebrospinal Fluid and Blood Flow in Mild Cognitive Impairment and Alzheimer's Disease: A Differential Diagnosis from Idiopathic Normal Pressure Hydrocephalus", BioMed Central, Fluids and Barriers of the CNS, 2011, 11 pages.

Johanson, Conrad, et al., "Periventricular Destabilization and Ventriculomegaly in Aging Rats: Implications for Reduced Neurogenesis and Cognition", SRHSB, http://www.srhsb.org/, 2009, 3 pages.

Lavinio et al., "Cerebrospinal fluid dynamics: disturbances and diagnostics." European Journal of Anaesthesiology, vol. 25, Supplement S42, Feb. 2008, pp. 137-141.

Marmarou, Anthony, et al, "A Nonlinear Analysis of the Cerebrospinal Fluid System and Intracranial Pressure Dynamics", J. Neurosurg, vol. 48, Mar. 1978, pp. 332-344.

Marmarou et al., "Compartmental analysis of compliance and outflow resistance of the cerebrospinal fluid system." Journal of Neurosurgery, vol. 43, Nov. 1975, pp. 523-534.

Modern Marvels Invent Now Challenge, Certificate of Recognition, 2006, 2 pages.

Radojicic, Milan, et al., "Ascending Central Canal Dilation and Progressive Ependymal Disruption in a Contusion Model of Rodent Chronic Spinal Cord Injury", BMC Neurology 7, No. 1, 2007: 30, 12 pages.

ISA/KR, PCT International Search Report and Written Opinion, Application No. PCT/US2012/070415, dated Apr. 10, 2013, 11 pages.

Korean Intellectual Property Office, ISA, "International Search Report and Written Opinion" in PCT Application No. PCT/US2013/037491, dated Sep. 23, 2013, 10 pages.

* cited by examiner

SYSTEMS AND METHODS FOR LUMBAR CEREBROSPINAL FLUID ACCESS AND TREATMENT

CROSS-REFERENCE TO RELATED APPLICATIONS

This patent application is a continuation-in-part of co-pending, non-provisional patent application Ser. No. 12/228,697 filed on Aug. 16, 2008, now U.S. Pat. No. 9,770,180 which claimed priority to non-provisional application Ser. No. 11/840,213 filed Aug. 16, 2007, now abandoned which in turn claims priority from provisional patent application 60/822,640, filed Aug. 17, 2006. This patent application also claims the benefit of the priority of provisional patent application 61/234,144 filed on Aug. 14, 2009. Each of the non-provisional patent application Ser. No. 12/228,697, the non-provisional application Ser. No. 11/840,213, the provisional patent application 60/822,640, and the provisional patent application 61/234,144 are incorporated herein by reference.

BACKGROUND OF THE INVENTION

This is directed to systems and methods for lumbar cerebrospinal fluid access, analysis, treatment, diversion and exchange.

The cerebrospinal fluid is a window to the functioning of the central nervous system. In humans, approximately 500 ml/day of cerebrospinal fluid is produced. The CSF circulates and traverses the brain and spinal cord several times a day and exhibits a craniocaudal flow pattern influenced by the cardiac cycle.

The cerebrospinal fluid can provide both diagnostic and therapeutic opportunities for treating brain and spinal cord injury and disease. Disease and injury of the cerebrospinal fluid may manifest as alterations in the production or absorption of cerebrospinal fluid, alterations in cerebrospinal flow and dynamics and/or the accumulation of toxins, metabolites and electrolytes in the fluid. Better diagnosis and therapeutics can therefore be achieved with systems and methods that improve the access, analysis, treatment, diversion and exchange of the cerebrospinal fluid.

Seemingly disparate brain and spinal disorders may be connected by disruptions in the normal cerebrospinal fluid. Thus systems and methods the improve the access, analysis, treatment, diversion and exchange of the cerebrospinal fluid can better address central nervous trauma, hemorrhage, infections, toxins, metabolic derangements, structural malformations, cystic lesions, benign and malignant masses, imbalances of cerebrospinal fluid production and absorption and flow, neurodegenerative diseases, pain syndromes and neuropsychiatric disorders, pharmacological studies on the CNS and experimental studies of the CSF dynamics.

The problem of chronic access for therapeutics to the central nervous system has heretofore been limited to subcutaneous cranioventricular reservoirs. The article "Implantable Devices for Chronic Access and Drug Delivery to the Central Nervous System" by Ommaya is incorporated herein by reference. It has been noted that these subcutaneous cranioventricular reservoirs are prone to infection, are prone to obstruction by biological material and can migrate unintentionally into brain regions important for speech, motor or vision, thereby creating new morbidity and mortality. In many ways, cerebrospinal fluid shunts are prone to the same problems. The article "Implanted ventricular shunts in the United States: The Billion-Dollar-A-Year Cost of the Hydrocephalus Treatment" by Patwardhan et al. is incorporated herein by reference.

I have also found that placement of this subcutaneous cranioventricular reservoir/pump requires general anesthesia which can be expensive. Additionally, placement of this type of device requires a cranial burrhole and ventriculostomy procedure which can be prone to complications and cosmetic concerns. The subcutaneous cranioventricular reservoir/pump also limits the volume of liquid that can be administered due to the sensitive cranial cerebrospinal fluid dynamics that occur within the fixed skull space.

The cranioventricular reservoir/pump only provides unidirectional flow of the cerebrospinal fluid due to the single catheter and reservoir/pump design, meaning that fluid can only be withdrawn or infused at a time and never simultaneously. Increasingly, the cerebrospinal fluid will be utilized to diagnose and treat disease, including the filtering of toxins and metabolites, which the present reservoir art will not allow. Furthermore, this art also lacks any monitoring, reporting and/or control ability. Finally, placement of this subcutaneous cranioventricular reservoir/pump necessitates repeating expensive imaging procedures such as CT or MRI. Repeat CT imaging can increase the radiation exposure to a patient.

Thus several advantages of one or more aspects are to provide a safer, faster and overall less expensive access to the cerebrospinal fluid. Other advantages of one or more aspects are to increase the comprehensive diagnostic and therapeutic capability. These and other advantages of one or more aspects will become apparent from a consideration of the ensuing description and accompanying drawings.

SUMMARY OF THE INVENTION

This is directed to chronically accessing the cerebrospinal fluid for diagnostics and therapeutics with an indwelling medical device by applying a lumbar intrathecal catheter tunneled to a subcutaneous dual reservoir/pump which can be accessed by an operator with needles. The subcutaneous dual reservoir/pump allows simultaneous, bidirectional cerebrospinal fluid access and flow and therefore cerebrospinal fluid exchange. The two chambers prevent mixing.

In some embodiments, two separate single lumen lumbar catheters, one for fluid inflow and another for fluid outflow, are coupled to the subcutaneous dual reservoir/pump.

In some embodiments, a single multilumen lumbar catheter is coupled to the subcutaneous dual reservoir/pump.

In some embodiments, the subcutaneous dual reservoir/pump is affixed by fasteners to the pelvis and accepts the tunneled lumbar intrathecal catheter.

In some embodiments, the subcutaneous dual reservoir/pump is placed subcutaneously in the lower abdomen and accepts the tunneled lumbar intrathecal catheter.

In some embodiments, the lumbar catheter and subcutaneous dual reservoir/pump assembly is coupled with other devices such as an external or subcutaneous drug pumps, cerebrospinal fluid pumps, anti-syphon technology, cerebrospinal fluid valves, cerebrospinal fluid dialyzers and/or filters.

In some embodiments, the lumbar catheter is coupled to at least one medical probe connected to a wire within the catheter that transmits information to I/O circuitry on the subcutaneous dual reservoir/pump. The medical probe can sense important physiological parameters.

In some embodiments, the catheter and subcutaneous dual reservoir/pump assembly contains a computational device that compares actual physiological data with expected values.

In some embodiments, the physiological parameters are sent to communications circuitry on the reservoir/pump, allowing telemetric transmittal of key physiological variables and broadcasting an alert or warning signal to the patient or medical personnel.

In some embodiments, the communications circuitry of the reservoir/pump can be programmed by medical personnel with the telemetric transmittal of commands, not limited to changing opening valve pressures.

In some embodiments, the catheter and subcutaneous dual reservoir/pump assembly has control circuitry and actuators that permit automatic interventions that bring the system toward homeostasis.

Therefore, the subject invention results from a realization that a safer, lesser invasive, comprehensive and overall less expensive strategy for chronic access to the cerebrospinal fluid is effected by a lumbar intrathecal catheter tunneled to a subcutaneous dual reservoir/pump assembly.

Figure 1:
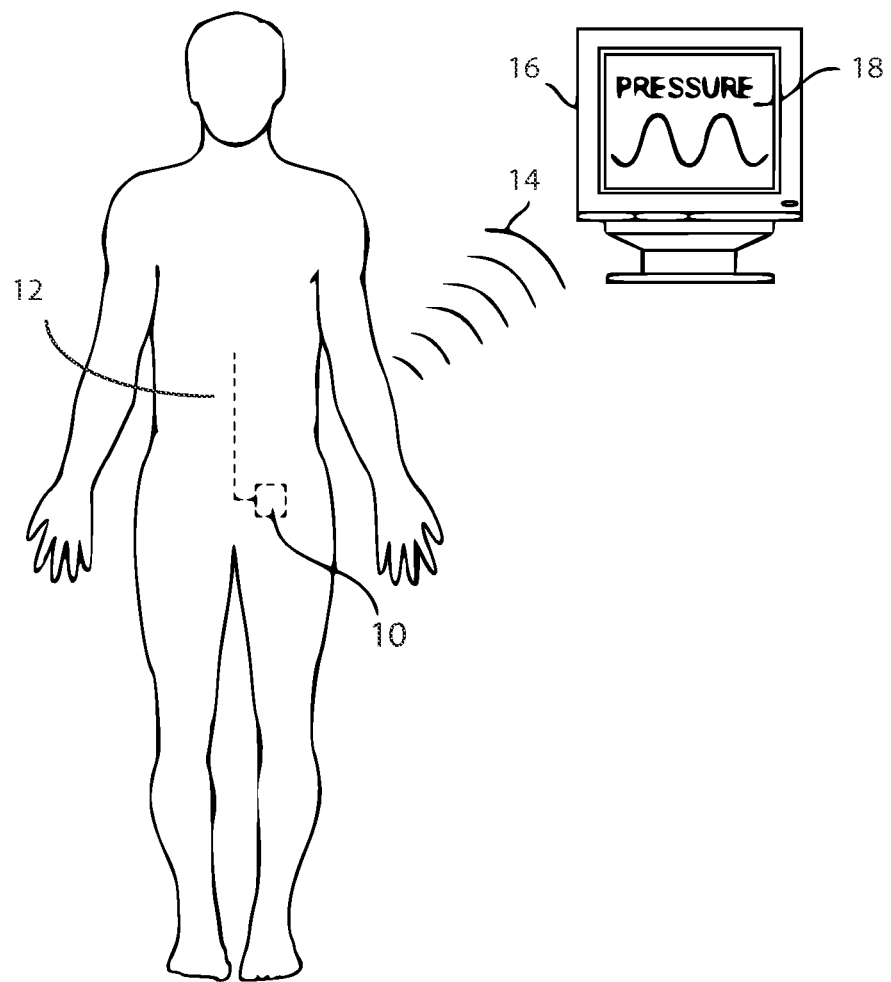
FIG. 1 is a diagram of a patient with implanted lumbar catheter coupled to medical probe sensing intrathecal pressure, the probe of which sends a wire to a subcutaneous dual reservoir/pump. The wireless transmitter on the assembly sends information on cyclical changes in the intrathecal pressure to an external display.

The following call a list of elements is consistently used throughout the drawings.

10 Wireless data transmitter
11 Subcutaneous dual reservoir/pump fastened to posterior ilium
12 Lumbar intrathecal catheter coupled with medical probe
13 L4/L5 interspace
14 Wireless data
16 Wireless data receiver
18 Wireless data display
19 Computational device algorithmic detection of falling glucose concentration over time
20 Subcutaneous dual reservoir/pump and computational device assembly
21 Fluid inflow reservoir and pumpable dome
22 Fastener to anatomic surface
23 Fluid outflow reservoir and pumpable dome
24 Catheter wire port connecting to embedded computational device surrounded by needle impervious material
26 Needle impervious material
27 Reinforced needle impervious base
28 Fluid inflow to catheter connector
29 Fluid outflow to catheter connector
30 Medical probe and wire along axis of catheter
32 Fluid outflow section
34 Fluid inflow section
36 Fluid outflow to reservoir connector
38 Fluid inflow to reservoir connector
40 Medical probe wire connector
42 Medical instrument 44 Fluid circuit
46 Energy waves
48 Diseased or injured tissue
50 Surgical tool
52 Computational device circuitry
54 Input/Output circuitry
56 Control circuitry
58 Communications circuitry
60 Memory
62 Storage
70 Inline inflow conduit
72 Inline outflow conduit coupled with check valve, flow meter and integrator
74 Pump and dialyzer assembly
76 Pump
78 Dialyzer
80 Check valve/flow meter
82 Valve which shunts fluid to optional conduit 84 when fluid volume and pressure high in system
84 Optional conduit to traditional distal shunt catheter toward drainage bag, peritoneum, pleura or atria
100 'Work' section at tip of catheter
200 'Bulk fluid exchange' middle section of catheter
300 'Connector' rear section of the catheter

DETAILED DESCRIPTION OF THE INVENTION

This is a system and method for treating neurological disease with an indwelling lumbar intrathecal catheter coupled to a medical probe and tunneled to a subcutaneous dual reservoir/pump that in an exemplary embodiment would be fastened to the posterior ilium.

The system and method allows for simultaneous inflow and outflow of cerebrospinal fluid, which would allow for treatment and exchange of cerebrospinal fluid. The system and method may be used in isolation or in line with other specialized devices such as internal subcutaneous valves, anti-syphon technology, pumps, drug delivery systems, filters and dialyzers. Alternatively, the dual dome subcutaneous reservoir/pump can be accessed by an operator externally with dual needles and external pumping, drug delivery, filtering and/or dialyzing of the cerebrospinal fluid may take place. The subcutaneous dual reservoir/pump allows simultaneous, bidirectional cerebrospinal fluid access and flow and therefore cerebrospinal fluid exchange. Finally, the system and method would allow for analysis of physiological data with an onboard computational device and allow for wireless transmission of physiological data and warning signals.

The system and method would allow for the wireless transmission of physiological data. FIG. 1 demonstrates a patient with an indwelling lumbar catheter with medical probe tunneled to a subcutaneous dual reservoir/pump. In this non-limiting example, the lumbar catheter is coupled to a pressure transducer at the tip of the catheter, which sends a wire along the catheter to the subcutaneous dual reservoir/pump which houses a computational device and circuitry which can transmit data wirelessly. Control circuitry allows the analysis of the data and the generation of warning signals in event the physiological data falls outside of expected norms. The wireless data 14 sent to a receiver 16 and then to a display 18. Changes in pressure and compliance are monitored and can be compared to norms, as well as computer modeled expected values. If the actual data falls outside the expected norm, as warning signal can be generated and sent wirelessly to the patient or medical personnel. Alternatively, an audible or tactile signal could be generated.

The medical probe of the system in an exemplary embodiment would house a pressure meter at this tip, which would move with the patient and not be subject to the positional reference changes that affect external transducers. The pressure meter could be a transducer, sensor and/or other microelectromechanical systems device. Other medical probe embodiments and combinations are possible. Medical probes could measure Ph, temperature, CSF gas values, oxygen, CO2, pressure, flow, volume infused and/or withdrawn, cerebrospinal fluid volume or impedance sensor, cardiac cycle, respiratory cycle, circadian rhythm, concentration of fluid, tonicity, osmolality, osmolarity, craniospinal compliance, cranial compliance, spinal compliance, a MEMS device where the lumbar catheter meets the dura monitoring dural pulsations and dural compliance, a conductivity sensor where the lumbar catheter meets the dura monitoring changes in dural conductivity with pulsations in the CSF and thus dural compliance, protein concentrations, glucose, lactate, bicarbonate, gyro-position sensor or gyroscopic sensors, amino acids, alpha ketoglutaric acid, magnesium ions, calcium ions, sodium ions, potassium ions, chloride ions, gamma amino butyric acid and other amino acid concentrations and electrical admittance/impedance between probes to gauge contact with tissue or catheter migration. Medical probes could also record the incoming ICP wave and via another coupled medical instrument feedback that waveform so as to produce standing waves.

Medical probes can also be visual guides, not limited to ultrasound transducers, cameras, infrared sensors, photoacoustic imagers with a plurality of light fibers surrounding the catheter, acoustic transducers. Data from medical probes could be processed by the computational circuitry to alert the patient or medical personnel or to cause actuators to enact changes to bring the system back to equilibrium.

Combinations of medical probes are possible including having the same probe at the tip and base of the catheter. With the latter, the signals from the respective probes could be compared to each other to cancel out noise, as well as be compared to an external signal. The pressure transducers in the intrathecal space register a pressure waveform that results from the cardiac pulsations. An external cardiac monitor, such as oximeter or other cardiac waveform analyzer such as an EKG or echocardiogram, could be co-analyzed with the intrathecal pressure measurements to cancel out noise. Moreover, a mathematical transfer function programmed into the embedded computational circuitry could produce expected intrathecal pressure waveform based on the expected cardiac output. This could be compared computationally to the actual waveform. Deviations from the expected could be used to alert the patient or medical personnel of the change. This data could also be used to signal embedded actuators to take a course of action to remedy the situation. In the non-limiting example of a fluid or drug pump in the intrathecal space, the intrathecal pressure follows a trajectory known as the compliance curve which represents the change in pressure which results from a change in volume of the system. Initially, small volume increases produces small pressure increases, but beyond a critical value, even small changes can produce dramatic increases in intrathecal pressure. Therefore, this system could be used to monitor the average intrathecal pressure vs. the pulse intrathecal pressure which tends to increase as the brain and spinal cord become less compliant. Thus computational circuitry could reduce the flow of fluid in the system as the compliance decreases. Alternatively, if the medical probe includes a volume sensor, the system could alert the needle for additional fluid pumping or alternatively could shut a outflow valve temporarily until the volume is increased endogenously through the natural cerebrospinal fluid production mechanisms. Additionally, it is known the intracranial/intrathecal spinal varies with physiological cycles and patient position. Thus, alternative embodiments of the system may include computational circuitry that identifies the components of the pulsatile intraspinal or intracranial pressure and then gate the opening of a cerebrospinal fluid valve according to the cardiac and/or respiratory cycle. The confluence of the cardiac and respiratory cycle peaks are thought to result in Lundberg C waves, which are transient spikes in intracranial and/or intrathecal pressure. Thus, if the volume of CSF were normal, the computational circuitry could temporarily shut a cerebrospinal fluid valve during the peak cardiac and respiratory activity to prevent overdrainage of the cerebrospinal fluid which is a known morbidity of the present art. Moreover, the computational device can compute the average intracranial or intraspinal pressure over time, adjust the valve automatically with actuators on the device and open the valve intermittently between episodes of the pulse ICP to prevent overdrainage. Gyroscopic sensors could also prevent overdrainage while the patient is recumbent by altering the valve opening pressure based on a patient's position. Computational circuitry could evaluate the components of ICP waveform to identify the position of the system along the compliance curve. Those skilled in the art know that three components of the waveform P1, P2 and P3 are recognized with the first being the percussive, the second being the tidal and third representing the dicrotic notch. Increases in the P2/P1 ratio as identified by the medical probe and computational circuitry would indicate lower compliance and would allow actuators to return the system to equilibrium, such as reducing the pump rate or increasing fluid egress, or alternatively notify a patient or medical personnel of the problem. Computational circuitry could monitor the beat to beat variation of the intracranial or intraspinal waveform and perform a fourier transform, which would identify the power in the respective harmonics. Increases in the power of the first harmonic of intracranial or intraspinal waveform would indicate lower compliance and could alert the patient or medical personnel or autonomously effect actuators to return the system to equilibrium such as reducing the inflow of fluid into the craniospinal system or increasing the outflow of the fluid from the craniospinal system or trigger a recalibration step of the equipment. Finally, although many features or descriptions described above can be in the context of a lumbar approach to the cerebrospinal fluid, it will be understood that features or descriptions can be applied to a variety of settings, including the cranioventricular, cisternal or venous sinus approaches. Thus monitoring the beat to beat variation of the intrathecal pressure could be used as a means of gauging the stability of the system and could guide therapeutic endeavors.

The dome design allows for access with a Huber-type needle as well as priming with finger ballotment but the improvement over prior art is that now bidirectional fluid inflow and outflow are possible, thereby allowing cerebrospinal fluid exchange.

Figure 2:
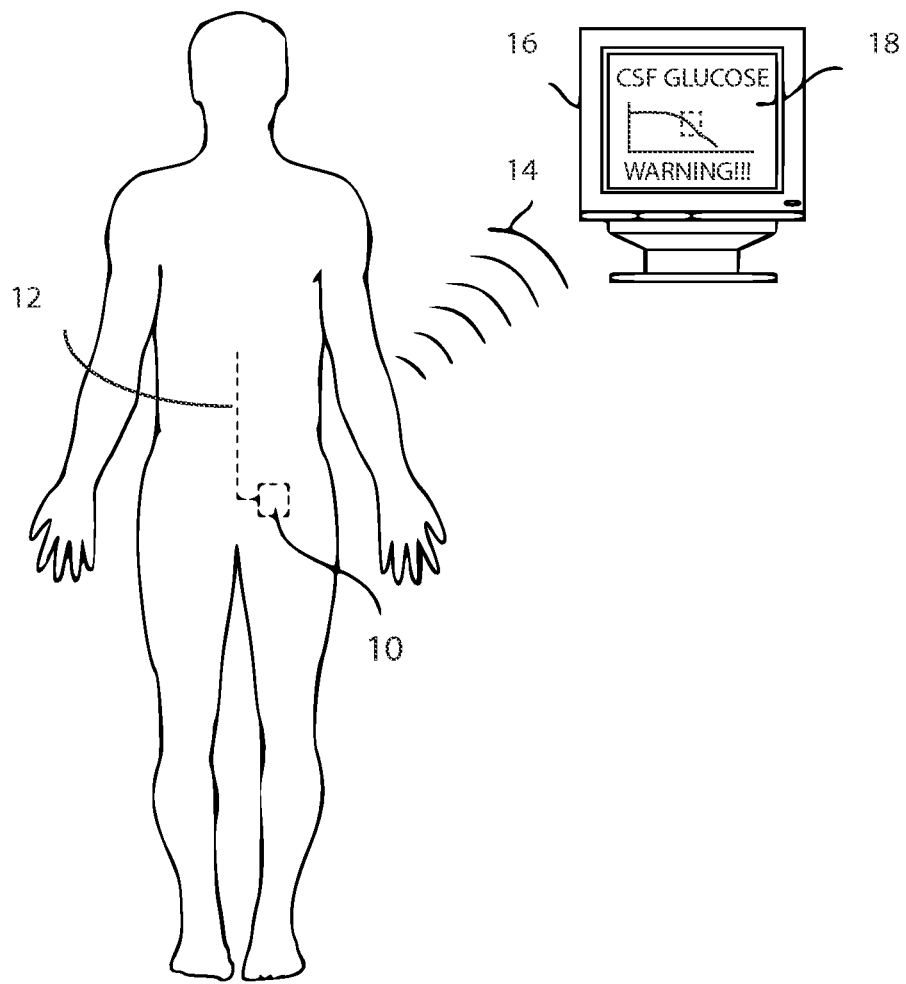
FIG. 2 is a diagram of a patient with implanted lumbar catheter coupled to a medical probe sensing cerebrospinal glucose, the probe of which sends a wire to a subcutaneous dual reservoir/pump. The wireless transmitter sends information on glucose concentration to a display. The control circuitry on the assembly sends a warning signal to a patient and/or medical personnel that an infection is imminent.
Figure 3:
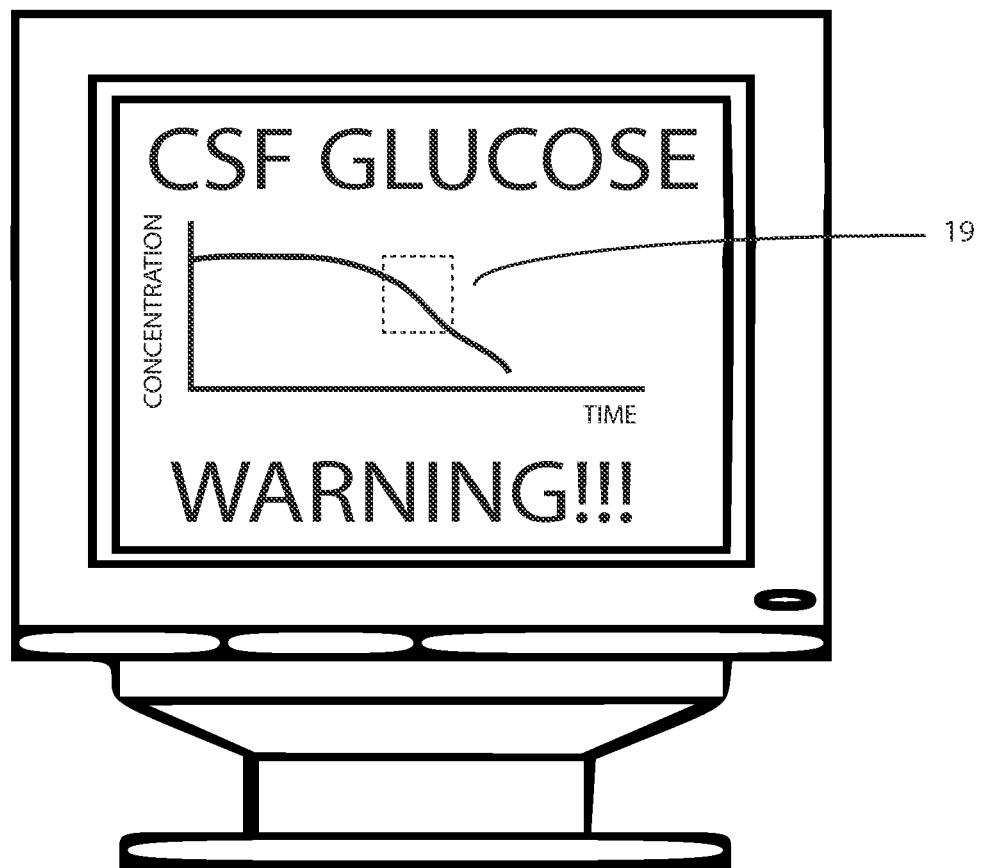
FIG. 3 is a magnification of the display in FIG. 1b. The display shows the concentration of glucose over time. An algorithm programmed into a computational device and control circuitry on the reservoir/pump assembly identifies an increasing rate of decrement in the glucose concentration of the cerebrospinal fluid and sends a wireless warning signal to a patient or provider.

FIG. 2 demonstrates an alternative embodiment where the lumbar catheter is coupled to a intrathecal glucose sensor. Changes in cerebrospinal fluid glucose concentrations are diagnostic of infections of central nervous system. Indwelling medical devices of the CNS are prone to infections. Currently, infections are dealt with after they have been initiated. This embodiment would allow the continuous or intermittent monitoring of CSF glucose values via a intrathecal glucose sensor. Any art recognized method of glucose sensing would be appropriate, not limited to enzymatic, ultrasound, conductivity, heat capacity, electrical stimulation, impedance spectroscopy, photoacoustic, spectrophotometry and/or optical. The medical probe would connect with a wire to the subcutaneous dual reservoir/pump which houses communication circuitry. The computation device could analyze the signal algorithmically, such as exemplified but not limited to FIG. 10, which shows one embodiment of such an algorithm. If a warning level is triggered, the patient or medical provided would be alerted with a wireless signal. Alternatively, an auditory or tactile signal can be enacted with built-in actuators. FIG. 3 demonstrates a higher magnification of one embodiment of the display a patient or medical provider would witness in event the computational device is alerted of a critical change in the cerebrospinal glucose concentration.

Figure 4:
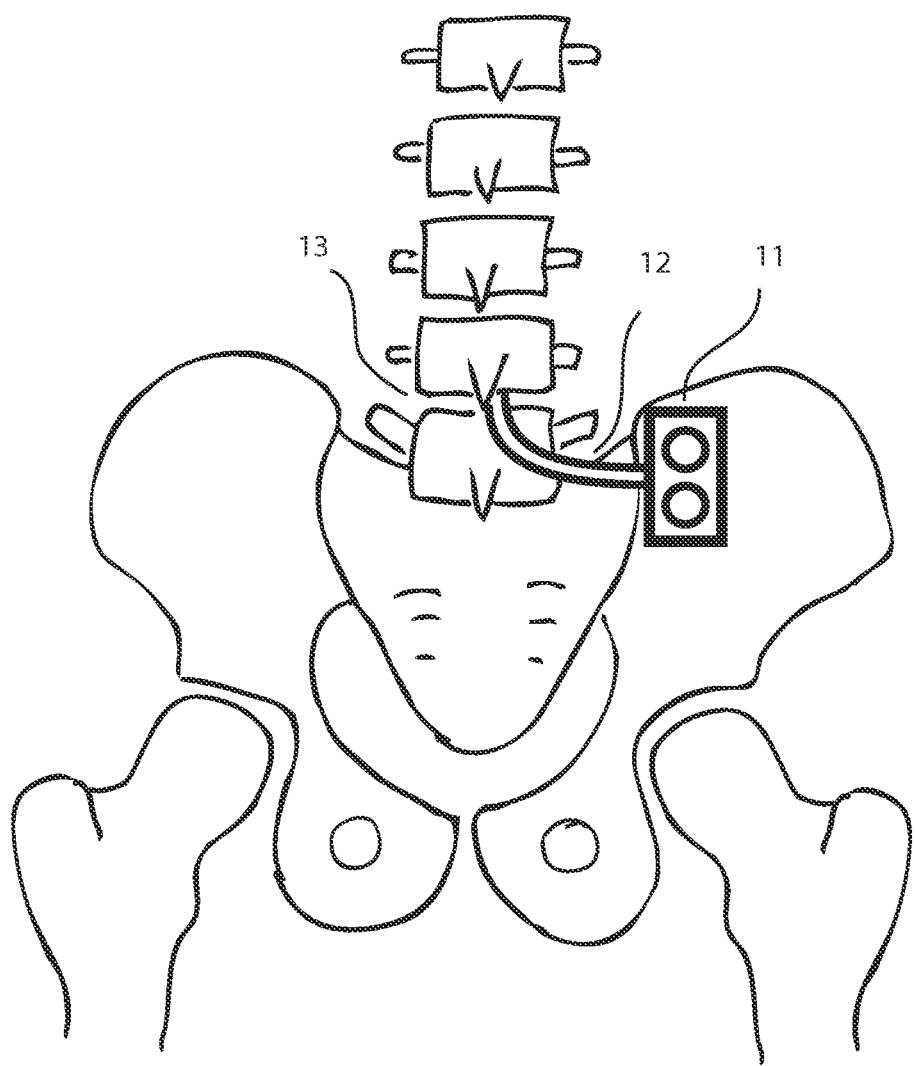
FIG. 4 shows the lumbar catheter and subcutaneous dual reservoir/pump fastened to the posterior ilium, which provides a convenient configuration for surgical implantation, tunneling and chronic access.

FIG. 4 demonstrates an exemplary embodiment of the anatomic placement and configuration of the system and method. A lumbar catheter coupled to a medical probe is placed in a lumbar interspace, preferentially the L4/L5 interspace. The catheter is tunneled to another location, an exemplary embodiment would be the posterior ilium. The ilium provides a convenient chronic access point along with a well-known anatomic landmark. The tunneling reduces infection and minimizes destruction of tissue. This placement is advantageous over the placement of an Ommaya cranioventricular catheter in that only local anesthesia would be necessary, along with less OR and recovery time. No cranial access is required, so there is less risk of catheter migration into the brain. Furthermore, the configuration is hid by the clothes, unlike the Ommaya, thus improving cosmesis. The lumbar location is also less prone to overdrainage of cerebrospinal fluid and is a natural reservoir for CSF, being more compliant to fluid infusion than brain and ventricles which are housed in fixed skull. Finally, the dual dome configuration of the subcutaneous reservoir/pump allows chronic access and simultaneous in and flow, which can be hooked up to dual needles and an external pump or dialyzer or filter for CSF exchange as well as continuous drug delivery. The dual dome configuration would provide a means to assess patency of the catheter tubing. Also the dual dome configuration would allow reversal of the pumping cycle to clear obstructions. An alternative embodiment could include an internal or external impeller to break up clot. The clot busting technology should break up debris to approximately 10 microns or less to allow aspiration, but minimize trauma to local structures. Other embodiments of anatomic placement include the subcutaneous lower abdomen or along the vertebral column, surgically fixed to a lamina or pedicle or other structural element of the vertebral column. The device may be fastened to an anatomic structure by any art recognized means not limited to screws, sutures, adhesive, etc. Radiopaque elements can be placed along any of the components to guide its evaluation with plain xray. Another advantage of this system and method is that it need require many repeat imaging examinations such as MRI and/or CT, which are costly and in the case of CT expose the patient to radiation.

Figure 5:
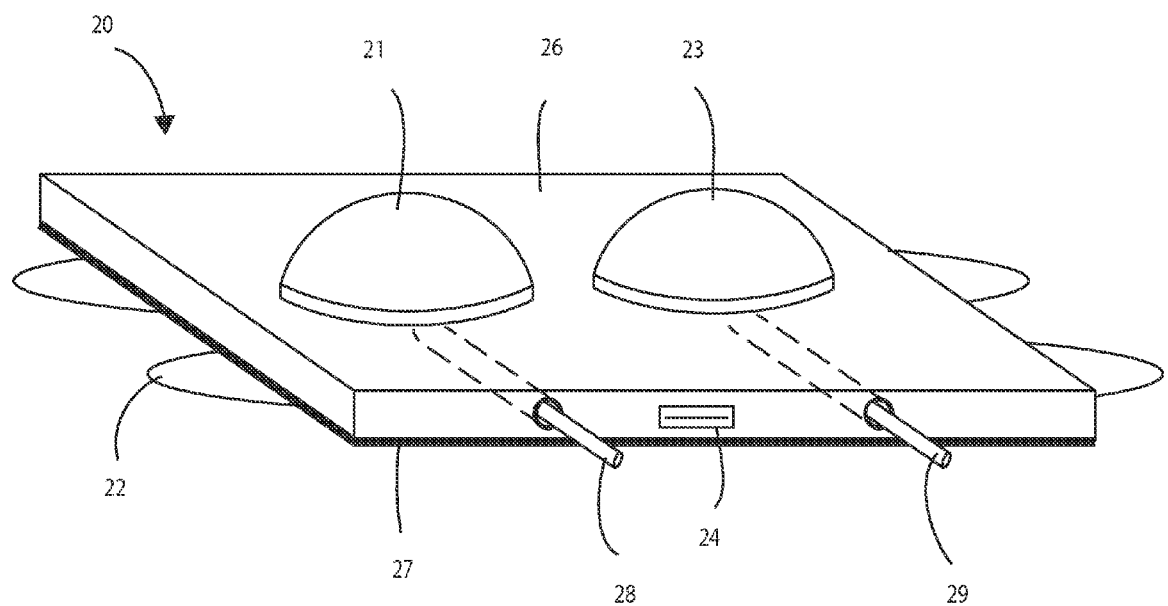
FIG. 5 shows the subcutaneous dual reservoir/pump. Two domes allow simultaneous inflow and outflow of fluid. Orientation of the domes may be vertical, horizontal or oblique. The in and out port can differ in shape or consistency to alert a practitioner which port is 'in' and which port is 'out.' A connector for the wire from the medical probe along with computational circuitry and wireless transmittal capability is housed in a needle impervious encasing. Fasteners are provided for affixing to an anatomic area and the bottom is additionally reinforced to prevent the needle from passing through the device or any inline fluid conduits which allow the device to be connected in series or parallel with other devices.

FIG. 5 demonstrates the subcutaneous dual reservoir/pump. The dome shape is exemplary but can be substituted in other embodiment by any suitable geometry. The domes should be made of a self-sealable material such as silicone. The body needs to be needle impervious because it houses sensitive electronics and computational circuitry. For strength, the housing can be reinformed with 26 and 27 with a casing of a suitable rigid biocompatible material not limited to polyethersulfone. Nitinol can be incorporated into any aspect of the assembly to prevent kinking. The catheter may also be segmented to prevent kinking or recoil and some embodiments would include a catheter that is steerable and lockable. Additional embodiment may be fitted an antibacterial filter or the component walls may be impregnated with an antibacterial coating. Additionally, the component walls, including catheter fluid apertures and fluid exchange sections may be treated and impregnated with antiproliferative medications, not limited to the immunosupressants such as cyclosporine or rapamycin, to reduce tissue ingrowth into the device. Also the dual dome configuration would allow reversal of the pumping cycle to clear obstructions. An alternative embodiment could include an internal or external impeller to break up clot. The clot busting technology should break up debris to approximately 10 microns or less to allow aspiration, but minimize trauma to local structures. Suitable tissue fasteners 22 allow the device to be permanently fastened to an anatomic site. An alternative, but less functional embodiment would only have a single dome reservoir/pump.

Figure 6:
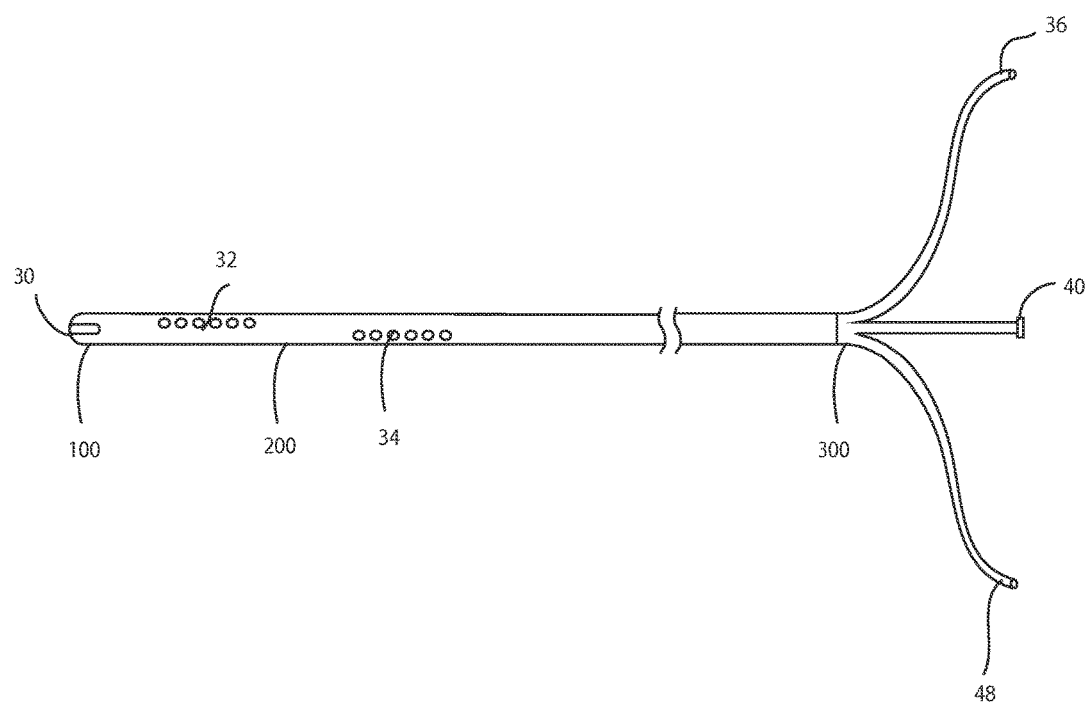
FIG. 6 shows the lumbar catheter coupled with a medical probe and simultaneous inflow and outflow capabilities. The catheter is made up of 3 sections, a distal 'work' section 100, an intermediate 'bulk fluid exchange' section 200 and a proximal 'connector' section 300.

FIG. 6 shows an exemplary embodiment of the catheter. A medical probe is coupled to the catheter, preferentially at the tip 30. Alternative embodiments may duplicate the same probe at another location on the catheter, such as the base. The signals from the probes could be compared to cancel noise and assess position of the catheter. Computational circuitry could effect actuators to bring the system back to equilibrium. The catheter is divided into a 'work' section 100, a 'bulk fluid flow/exchange' section 200 and a rear 'connector' section 300. The 'work' section in this exemplary embodiment consists of a medical probe at the tip. Alternative embodiments would allow additional intervention, including end fire fluid ports capable of pulsatile or oscillatory flow, along with surgical tool ports. The 'bulk fluid flow/exchange' section consists of a plurality of apertures and allows for more than one fluid exchange section which can be separated by a distance to prevent remixing of the clean or desired fluid after treatment. The catheter is some embodiments is segmented or can contain motile elements for steering, maneuvering and locking without recoil. Aspects of the catheter can be reinforced with nitinol to prevent kinking Additional tool ports and/or medical instruments can be placed along the 'bulk fluid flow/exchange' section. The rear section in this exemplary embodiment includes inflow 38 and outflow 36 and an electrical connector 40 which connects the wire from the medical probe to the embedded computational circuitry of the subcutaneous dual reservoir/pump.

Figure 7:
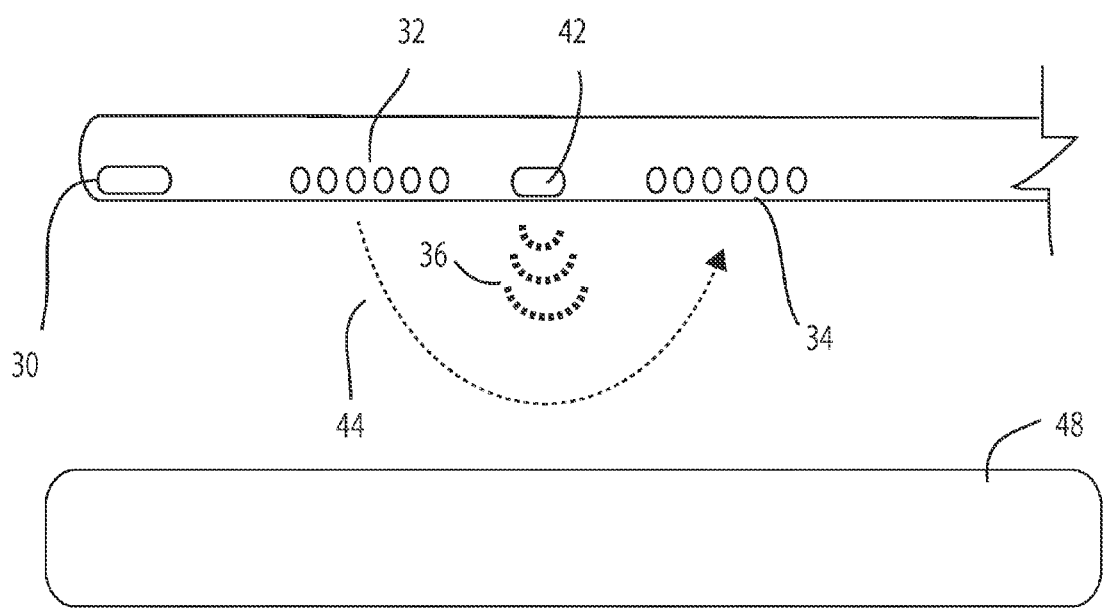
FIG. 7 shows the lumbar catheter with medical probe at the tip. This medical probe can be used to navigate the catheter by forward looking or side-fire linear orientation. The 'bulk fluid exchange' section 200 is fitted with 2 side fire fluid exchange sections, one for outflow and one for inflow. Between the fluid exchange sections is another medical instrument for transmitting or receiving energy. This configuration should not be limited to photoactivation of medications, cooling of tissue that may be heated by the medical instrument or fluidic pulses to counteract negative pressure and microbubble formation by the medical instrument.

FIG. 7 demonstrates an alternative embodiment of the 'bulk fluid flow/exchange' section where a medical instrument has been incorporated between two fluid exchange sections. This configuration would not be limited to the photoactivation of medications, cooling of tissue that may be heated by the medical instrument or fluidic pulses to counteract negative pressure and microbubble formation by the medical instrument. The medical instrument can occur anywhere along the catheter and send and receive energy in any art recognized form not limited to acoustic, radiofrequency, ultrasonic, high frequency ultrasound, photoacoustic, infrared, infrared differential interference contrast, visible light, laser, raman spectroscopy, optical coherence tomography, The fluid circuit can vary the volume infused over time, as well as the temperature and concentration of fluids which can be timed and coupled to energy pulses, thereby allowing novel combination therapies. Energy can be delivered at a resonant frequency of a target at desired power and duration, including sweeping above and below that frequency until a desired effect is achieved, such as eradication of an infection or tissue growth.

Another embodiment of this system with a steerable catheter would include fiducial adhesives that are placed on a patient along key anatomic landmarks of the head, neck, shoulders and pelvis. After imaging with the fiducials, the data is fed into a computer with imaging data along with surface fiducial landmarks. Thereafter, fiducials emitting energy toward the spinal or cranial pathway can be placed on the initial adhesive (e.g, when MRI makes the metal containing fiducials incompatible). These sonic fiducials can transmit energy that can be picked up by one of the medical probes on the catheter, which then will be fed to the computational device and computer, along with original imaging to get a sense of the position of the catheter. This can reduce the amount of radiation a patient experiences due to repeat fluoroscopy.

Figure 8:
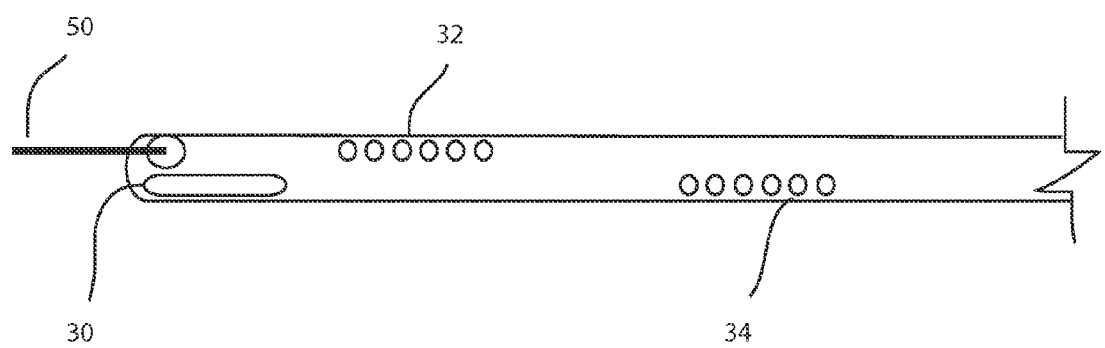
FIG. 8 shows the lumbar catheter coupled to a medical probe at the tip with the addition of an endfire aperture and lumen. A lumen is a hollow tube along the axis of a catheter which may transmit a solid body (not limited to an electrical wire, guidewire or surgical tool), liquid or gas. This endfire aperture and lumen of the 'work' section is acting as a sheath to introduce another surgical tool. The medical probe can be used to visualize the activity of the surgical tool.

FIG. 8 demonstrates another embodiment of the catheter with an end fire aperture and lumen acting as a sheath to pass another surgical tool. The surgical tool can be visualized with the medical probe, as well as the surrounding tissue to prevent any injury. If the surgical field is bloody, a plain camera could not visualize very much, so a modality with depth such as ultrasound would be helpful. The surgical tool should not be limited to microscissors, microscalpel, needle, laser, electrothermy, radiofrequency ablation, suturing tools, microneedle, xray device, brachytherapy pellet, RF generator, microwave generator, acoustic generator, cryablation laser or other cause. Although many features or descriptions described above can be in the context of a lumbar approach to the cerebrospinal fluid, it will be understood that features or descriptions can be applied to a variety of lesser invasive surgical approaches, including acute surgeries applied to but not limited to the cranioventricular, cisternal or venous sinus approaches. Moreover, the features or descriptions can be applied to other body vessels, lumens, cavities and tissues for lesser invasive diagnostics and therapeutics.

Figure 9:
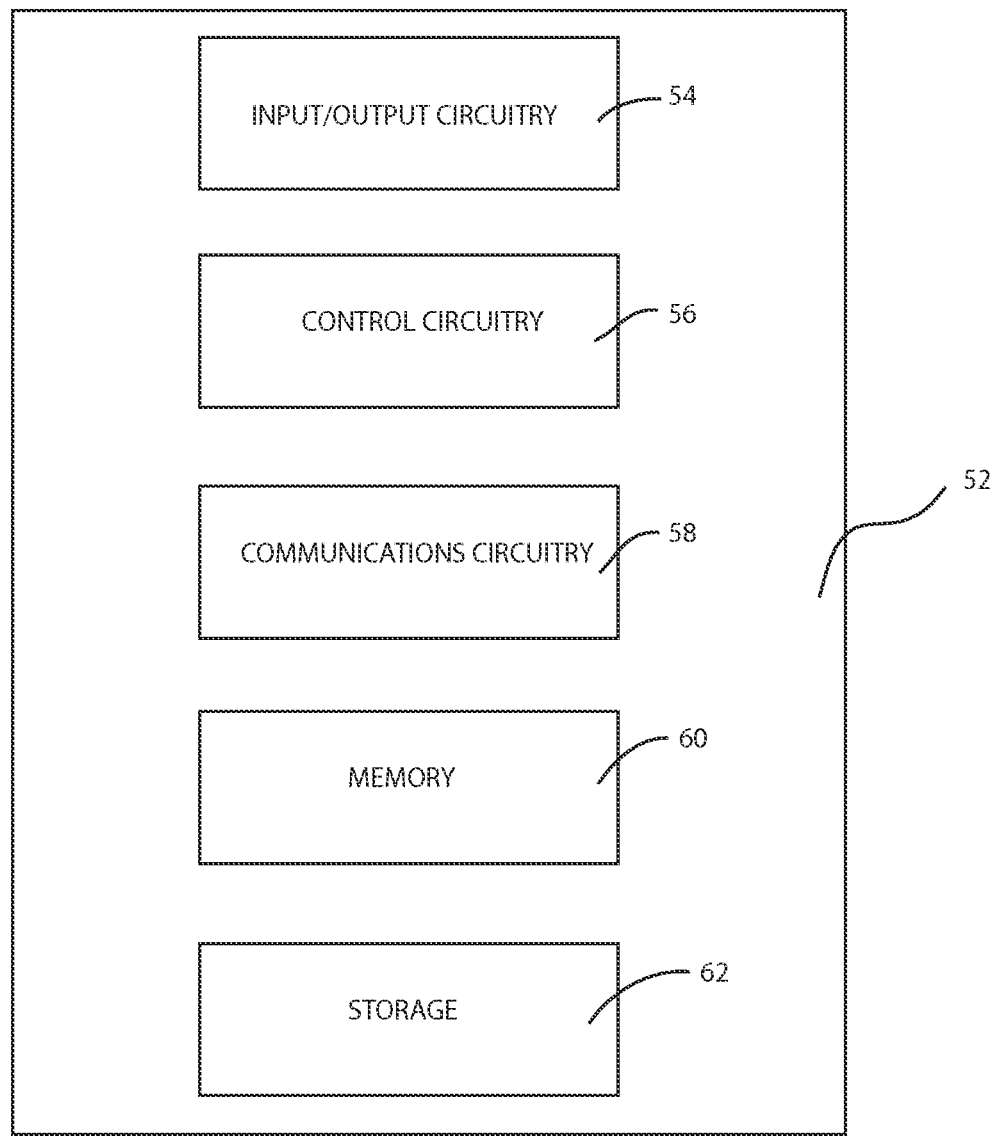
FIG. 9 shows the computational circuitry which can be coupled to or embedded on the subcutaneous dual reservoir/pump. The circuitry can be protected with a needle impervious and water resistant sleeve material to prevent damage.

FIG. 9 demonstrates the computation circuitry of the device which incorporates input/output circuitry, control circuitry, communications circuitry, as well as memory and storage. The computational device can be embedded with mathematical models of the desired system and actual measured parameters can be judged against expected values. Deviations from the norm would be sent to the patient or medical provider. The computation circuitry can send telemetric data to alert a patient or provider of warning signals. Moreover, the computation device can receive signals from the medical provider in order to change variables and actuators, not limited to the opening pressure of a shunt valve or simply to query stored historical data. The access should be password protected.

Figure 10:
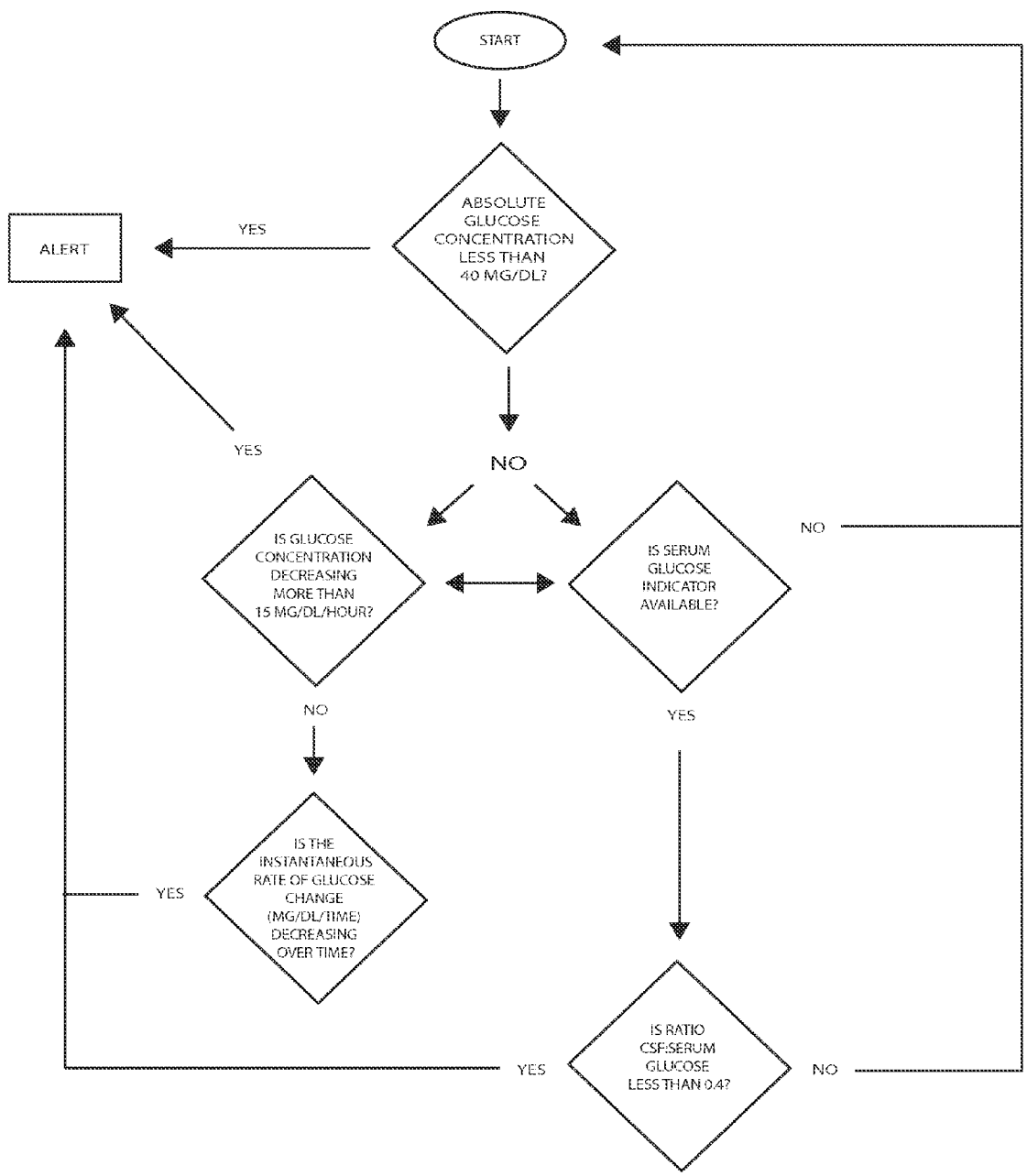
FIG. 10 shows one embodiment of an algorithm that is programmed into the control circuitry of the computational device when the catheter is coupled to a cerebrospinal glucose sensor. This allows for monitoring and reporting of changes in cerebrospinal fluid glucose concentration, which can predict infections in the cerebrospinal fluid. The algorithm allows the computational device to notify the patient or medical personnel of an impending infection.

FIG. 10 demonstrates a algorithm for the analysis of the cerebrospinal glucose concentration which is important variable when assessing for infection. The system and method would allow for the continuous and intermittent measurement of CSF glucose values and the reporting of any critical changes. The system and method would also allow for the comparison of CSF glucose values to an external non-CSF source via telemetric data, allowing the computation of a CSF:serum ratio, whereby a value lower than 0.4 notifies a patient or medical personnel. Tables can be adjusted in the cases of newborns, where a ratio below 0.6 is considered abnormal.

Figure 11:
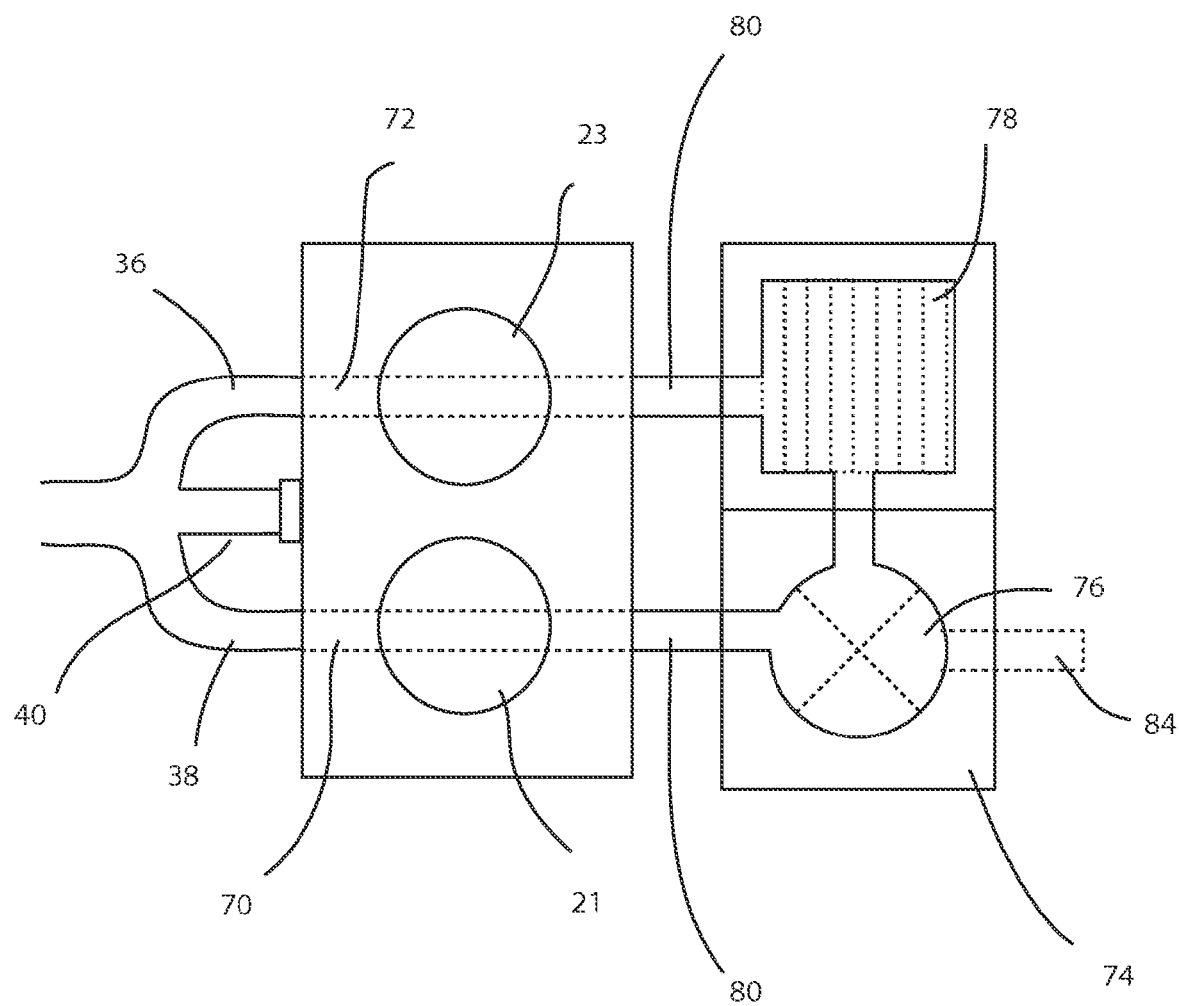
FIG. 11 shows one embodiment of the lumbar catheter and subcutaneous dual reservoir/pump coupled to another medical device, which in this instance is a cerebrospinal fluid pump and dialyzer.

FIG. 11 demonstrated an alternative embodiment of the system and method whereby the lumbar catheter with medical probe and subcutaneous dual reservoir/pump assembly are coupled with another medical device, not limited to a CSF pump, filter, dialyzer, valve, drug pump, etc. The devices can be placed in series or parallel. FIG. 11 shows how a CSF pump and dialyzer assembly can be added to subcutaneous dual reservoir/pump system. Feedback from the medical probe can guide the computational circuitry on when to opening up the valves 72 and 80. The valve could check the flow of fluid as it is known to those skilled in the art that constant infusion tests have demonstrated that patients tolerate low flows up 0.76 ml/min, so this could be a target for net flow rate. For example, in the medical probe is detected a change in ph or increasing concentration of certain metabolites (e.g., beta amyloid), then pump/dialyzer 76 would start working. If a volume sensor/medical probe detects low volume, the pump would stop to prevent overdrainage and could alert the patient or medical personnel. An alternative embodiment would add an additional fluid conduit 84 (similar to 70 and 72) but this time through the pump/dialyzer 76 toward another catheter which would feed into a drainage bag or simply drain into the peritoneum, the pleura or atrium. This pathway would be actuated by closing valve 82 when the volume sensor indicates increased pressure and volume in the craniospinal compartment. This system comprises a novel and intelligent shunting mechanism. The application of this technology is improved with medical probe on the CSF catheter and the computational circuitry on the dual dome reservoir/pump which otherwise has no moving parts to interfere with circuitry. The circuitry is also housed in a needle impervious casing. Additionally, the dual dome system could be utilized to reverse the pumping cycle to remove obstructions of the catheter. Additionally, accessing the system with two needles would allow one to assess the patency of the component catheters by passing a signal through the tubes and assessing the response.

Although many features or descriptions described above can be in the context of a lumbar approach to the cerebrospinal fluid, it will be understood that features or descriptions can be applied to a variety of lesser invasive surgical approaches, including acute surgeries applied to but not limited to the cranioventricular, cisternal or venous sinus approaches. Moreover, the features or descriptions can be applied to other body vessels, lumens, cavities and tissues for lesser invasive diagnostics and therapeutics.

While the above description contains many specificities, these should not be construed as limitations on the scope of the invention, but as exemplifications of the presently preferred embodiments thereof. Many other ramifications and variations are possible within the teaching of the invention. Additionally, any combination of the above examples may be possible. Thus the scope of the invention should be determined by the appended claims and their legal equivalents, rather than the examples given.

What is claimed:

1. An implantable system for chronic access to cerebrospinal fluid, said system comprising:
A multilumen bidirectional fluid flow catheter configured for chronic implantation and placement along a cerebrospinal fluid pathway, wherein said multilumen bidirectional fluid flow catheter comprises a plurality of fluid outlets, and a plurality of fluid inlets
said multilumen bidirectional fluid flow catheter configured to connect, via tunneling, to an assembly comprising at least one finger pumpable dome configured for chronic subcutaneous implantation, each said at least one finger pumpable dome having dual functions of fluid reservoir and pump;
wherein said multilumen bidirectional fluid flow catheter and said at least one finger pumpable dome are further configured to allow simultaneous, bidirectional, cerebrospinal fluid access and cerebrospinal fluid exchange.

2. The system of claim 1, wherein the multilumen bidirectional fluid flow catheter is configured to be chronically implanted in a lumbar interspace.

3. The system of claim 1, wherein said assembly further comprises a fastener to an anatomic surface that is further configured to be chronically implanted by subcutaneous fastening to a patient's pelvis.

4. The system of claim 1, wherein said multilumen bidirectional fluid flow catheter further comprises a medical sensor.

5. The system of claim 4, wherein said medical sensor is configured to measure intrathecal pressure.

6. The system of claim 1, wherein said assembly further comprises a computational device.

7. The system of claim 6, wherein said computational device is configured to wirelessly transmit physiological data and warning signals to a patient or provider.

8. The system of claim 6, wherein said computational device is further configured to wirelessly accept commands from a medical provider.

9. The system of claim 1, wherein said multilumen bidirectional fluid flow catheter further comprises, between said plurality of fluid outlets and said plurality of fluid inlets, a medical instrument for transmitting or receiving energy;
said energy comprising any of acoustic, radiofrequency, ultrasonic, high frequency ultrasound, photoacoustic, and infrared energy.

10. The system of claim 1, wherein said assembly is further configured in a needle impervious base to form a unit configured for subcutaneous implantation, and;
wherein said at least one finger pumpable dome is further configured to enable, while positioned subcutaneously, for chronic access by needle.

11. The system of claim 10, wherein said needle impervious base further comprises a wireless transmitter and computational circuitry.

12. A system of cerebrospinal fluid diversion comprising:
a multilumen bidirectional fluid flow catheter coupled to a medical sensor for measuring pressure of cerebral spinal fluid;
said multilumen bidirectional fluid flow catheter configured to connect, via tunneling, and via an internal subcutaneous valve to an assembly comprising at least one finger pumpable dome configured for chronic subcutaneous implantation, each said at least one finger pumpable dome having dual functions of fluid reservoir and pump;
said assembly further comprising a computational device;
wherein said internal subcutaneous valve is also coupled to said computational device, and wherein said computational device is configured to receive said pressure measurements from said medical sensor, identify components of pulsatile pressure, and modulate said internal subcutaneous valve to prevent overdrainage of the cerebrospinal fluid.

13. The system of claim 12, wherein said medical sensor is further configured to measure volume.

14. The system of claim 12, wherein said medical sensor is further configured to analyze a fluid composition of said cerebrospinal fluid.

15. The system of claim 12, wherein said valve is programmable.

* * * * *